United States Patent

Ohm et al.

Patent Number: 4,966,772
Date of Patent: Oct. 30, 1990

[54] DHP DELAYED RELEASE PREPARATION

[75] Inventors: Andreas Ohm, Neuss; Helmut Luchtenberg, Niederkassel; Manfred Bücheler, Overath; Roland Rupp, Leichlingen; Heinrich Feltkamp, Hennef, all of Fed. Rep. of Germany

[73] Assignee: Bayer Aktiengesellschaft, Leverkusen, Fed. Rep. of Germany

[21] Appl. No.: 336,961

[22] Filed: Apr. 12, 1989

[30] Foreign Application Priority Data

Apr. 29, 1988 [DE] Fed. Rep. of Germany ....... 3814532

[51] Int. Cl.$^5$ ................................................ A61K 9/36
[52] U.S. Cl. ..................................... 424/482; 424/480; 424/470; 424/471; 424/472; 424/479
[58] Field of Search ............... 424/474, 479, 480, 482, 424/469, 470, 494, 497

[56] References Cited

U.S. PATENT DOCUMENTS

| | | | |
|---|---|---|---|
| 4,267,138 | 5/1981 | Dobo et al. | 424/494 |
| 4,309,405 | 1/1982 | Guley et al. | 424/493 |
| 4,758,437 | 7/1988 | Sonobe et al. | 424/501 |
| 4,765,990 | 8/1988 | Sugimoto et al. | 424/494 |
| 4,800,084 | 1/1989 | Zerbe | 424/474 |
| 4,808,413 | 2/1989 | Joshi et al. | 424/458 |

FOREIGN PATENT DOCUMENTS 0142561  5/1985  European Pat. Off. .

OTHER PUBLICATIONS

Conte et al., "Press-coated, zero order drug delivery systems," I1 Farmaco, No. 3 (Mar. 1984), pp. 67–75.
Salomon et al., "Sustained release of a water-soluble drug . . .", Pharmazeut. Ind., vol. 41, 1979, pp. 799–802.

*Primary Examiner*—Thurman K. Page
*Assistant Examiner*—James M. Spear
*Attorney, Agent, or Firm*—Sprung Horn Kramer & Woods

[57] ABSTRACT

A solid medicament preparation having long-lasting action containing a sparingly soluble dihydropyridine active compound of the Formula (I)

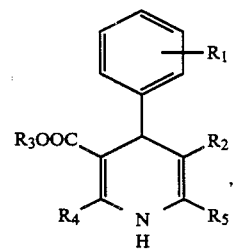

the preparation having a core-coating construction, the core containing at least one of the above mentioned dihydropyridines in slow-release form, the inner-most coating situated around the core contains no active compound and only dissolves slowly and adjacent to the inner-most coating a rapid release initial dose of the active compound mixed with a polymer.

3 Claims, 1 Drawing Sheet

DHP DELAYED RELEASE PREPARATION

The invention relates to solid medicament preparations consisting of a core and a coat applied thereto and having a long-lasting action for dihydropyridines, and processes for their preparation.

Active compounds from the dihydropyridine class of substances and their use as circulatory agents have already been disclosed (compare Brit. Pat. No. 1,173,862, Brit. Pat. No. 1,358,951, U.S. Pat. No. 4,256,749, German Offenlegungsschrift No. 3,311,003 and U.S. Pat. No. 4,264,611). In the galenical preparation of these potent active compounds, difficulties frequently occur since the substances only have a very low solubility, are frequently light-sensitive and their absorbability in biological systems frequently leads to problems.

Numerous experiments have been undertaken to produce optimum galenical preparations which improve the bioavailability of these potent active compounds. Thus, for example, some active compounds have been dissolved in specific organic solvent systems and filled into gelatin capsules in order to ensure a rapid and effective onset of action (compare Brit. Pat. No. 1,362,627). The conversion of dihydropyridines such as nifedipine into co-precipitates or "solid solutions" using water-soluble polymers in order to improve the bioavailability has also been investigated (compare Brit. Pat. No. 1,579,818). However, using these galenical preparations, no reduction in intake to once to a maximum of twice daily can be achieved with the dihydropyridines mentioned, inter alia.

For the treatment of diseases which have to be treated over relatively long periods of time, such as, for example, hypertonia and angina pectoris, it is desirable to keep the frequency of intake of medicaments as low as possible. This is not only more agreeable to the patient, but it also increases the safety of treatment, in that it reduces the disadvantages of irregular intake and stabilizes the active compound concentration present in the body. In this way, the risk of undesired over- or underdosage is minimized at the same time (peak blood levels of the active compound occur rapidly after intake from releasing administration forms or, with a higher administration frequency, on irregular or forgotten intake).

Of particular advantage are administration forms which release the active compound corresponding to the needs of the patient.

Thus, for example, a diurnal rhythm is described for the course of the blood pressure (Lemmer, B. in: Chronopharmakologie, Tagesrhythmen und Arzneimittelwirkung (Chronopharmacology, diurnal rhythms and medicament action), Wiss. Verl. GmbH, Stuttgart 1984): during the night both normo- and hypertonic values (systolic and diastolic) fall to a minimum (towards 04.00 hours), to climb steeply again after that in the early hours of the morning (also during the sleep)((blood pressure maximum towards 10.00 hours). A blood pressure medicament suited to the diurnal rhythm accordingly should have the advantage compared to conventional delayed release systems of only supplying the patient with active compound when active compound is required. In particular, the steep rise in blood pressure in the early hours of the morning can be safely checked by the release of disproportionately high amounts of active compound in spite of the sleep of the patient, without supplying the body in the times with a falling off of blood pressure with active compound which is not then required (example: evening (nightly) intake, placebo phase during the falling off of blood pressure, beginning of release of active compound in the early hours of the morning).

The like also applies to angina pectoris: in patients with stable angina pectoris or with Prinzmetal angina pectoris time-dependent differences in the ECG and in the frequency of onset can be detected under corporeal loading. Epidemiological studies have shown that the frequency distribution of cardiac infarct attacks is subject to a diurnal rhythm. Cardiac morbidity thus exhibits a maximum in the early hours of the morning.

Both for the doctor and for the patient, a requirement exists, for example for the long-term therapy of cardiac circulation disorders, to get the highly active dihydropyridines into an available form in which a once daily administration suffices for disease treatment. Medicament preparations having relatively retarded release of active compound (delayed release forms) have already been described for dihydropyridines. Thus the production of a slow-release preparation has been investigated, for example, by means of a specific particle size distribution of the crystalline active compound or by means of a selected specific surface area of the active compound crystals (compare German Offenlegungsschrift No. 3,033,919). Furthermore, specific tablet preparations have been proposed which, according to the principle of the osmotic pump, release the active compound from the interior of the tablet, which is surrounded with a semipermeable lacquer layer, over a relatively long period of time through a previously defined opening and thus attain a delayed release effect (compare U.S.-PS NO. 3,916,899).

The previously known preparation forms having relatively delayed release of active compound, in particular those for dihydropyridines, exhibit a series of disadvantages. Their delayed release action is only limited to a few hours, so that the patient as a rule, as previously, has to administer twice or more times daily; after several hours the rate of release of the active compound slackens considerably so that even the blood level can fall beneath the necessary limit of effectiveness.

In the abovementioned osmotic system, local irritations of the tissue can occur in the stomach or intestinal tract, depending on the capsule filling employed, owing to an excessive concentration of active compound.

Due to the nature of the osmotic system, a part of the active compound can remain in the medicament form and thus not be available for the desired absorption. Moreover, the production of this medicament form is very complex since in this case organic solvents have to be employed in the production process and the lacquer layer of each tablet has to be bored through with the aid of a laser beam.

In all previously described delayed release medicament forms, an adjustment of the release of active compound to diurnally rhythmic biological events (for example blood pressure) and pathological events (pathological ECG changes, angina pectoris attacks) is not possible (on single dosing). Lacquering with a gastric juice-resistant coating which causes a part or the whole dose to be released from the medicament form after leaving the stomach (discontinuously releasing delayed release form) is already unreliable for reasons of the pH dependence of the liberation of active compound, since the dwell times in the stomach vary enormously from patient to patient and, moreover, depend on the absorption of nutrient (dwell times in the stomach about 0.2-12 hours). With such a medicament form, the release of a part to the medicament substance can be delayed temporarily: however, the reproducibility of this lag time is not given by the abovementioned reasons so that, for example, a safer adaptation to diurnal rhythmdependent biological processes cannot thus be achieved.

It has now been found that solid medicament preparations consisting of a core and a coat applied thereto having a long-lasting action, and which contain a sparingly soluble dihydropyridine active compound, in particular of the general formula I

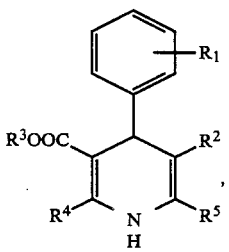

in which $R^1$ stands for one or two identical or different substituents from the group comprising nitro, halogen, trifluoromethyl or $OCHF_2$ or in which

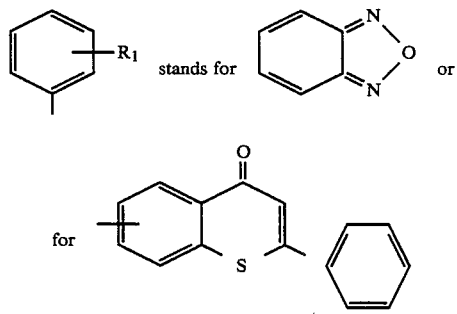

$R^2$ stands for a nitro group or for the radical $COOR_6$, where $R_6$ denotes alkyl having 1 to 10C atoms which is optionally substituted by alkoxy having 1 to 4 carbon atoms or by one or more halogens or where $R^2$ together with $R^5$ stands for the lactone group $-CO-O-CH_2-$, $R^3$ stands for alkyl having 1 to 10 C atoms, which is optionally substituted by alkoxy having 1 to 4 C atoms or by one or more fluorines and $R^4$ and $R^5$ are identical or different and in each case stand for alkyl having 1 to 4 C atoms, which is optionally substituted by hydroxyl, where the core-coat administration form (a) comprises a core which contains at least one of the abovementioned dihydropyridines in slow-release form and (b) comprises a coat situated around the core which contains no active compound and which only dissolves slowly, and (c) if desired, additionally containing on the coat, a rapid-release initial dose of the active compound with a diameter of the form being between 0.5 and 15 mm show surprising effectiveness.

Those preparations may be mentioned as preferred which contain 10 % to 100 %, preferably 50 % to 100 %, of the total dihydropyridine active compound of the administration form in the core.

Depending on the type of active compound, the preparations according to the invention preferably contain in total 1 to 200 mg, in particular 10 to 150 mg, of at least one active compound from the dihydropyridine class.

The slow-release core of the preparation preferably contains the active compound in finely ground or micronized crystalline form.

Cores having slow release are preferably taken to mean those cores which contain the active compound in delayed release form and release it to less than 75 % in a time of one hour/test conditions correspond to the specification for solid formulations of the active compound, for example for nifedipine, nitrendipine, nimodipine and nisoldipine: according to one of the conditions mentioned below: Condition A: USP paddle, 4 l of synthetic gastric juice without pepsin plus 0.1 % Tween 80, 100 rpm, Condition B: USP paddle, 0.9 l of 0.1 N hydrochloric acid plus 0.25 % of Texapon K12, 100 rpm, 37° C., Condition C: USP paddle, 0.9 l of methanol/water (40:60), 50 rpm, 37° C.

The retardation of the release of the core can be carried out by the customary methods (for example nifedipine according to U.S. patent application Ser. No. 294,608, filed Aug. 20, 1981, now abandoned (EP-B No. 47899), or other methods corresponding to the prior art.

The coat contains no active compound. Mixed with pharmaceutically customary auxiliaries such as, for example, lactose, starch, cellulose and citric acid, inter alia and magnesium stearate as a lubricant, the coat material forms a hydrophilic gel-forming polymer. This hydrophilic polymer controls the dissolution rate and erosion of the coat. Control factors for the dissolution-/erosion rate of the coating material are, inter alia, the layer thickness of the coat and the ratio polymer(s)-/residual auxiliaries.

Suitable hydrophilic gel-forming polymers are, for example modified starch and/or cellulose-like substances such as methylcellulose, hydroxypropylmethylcellulose, hydroxypropylcellulose and sodium carboxymethylcellulose.

The erosion and dissolution rate of the coat can also be controlled via the different degrees of viscosity of the polymer, in which case the rate is increased if low viscosity qualities are employed and is slower with the employment of high viscosity types. Customarily, the concentration of the polymer in the coating material is 5-100 %, preferably 25-90 %. The concentration employed is dependent on the degree of viscosity of the polymer(s) and on the solubility/hydrophilicity of the auxiliaries employed and the amount thereof.

Customary known galenical measures such as, for example, lacquering the core with a gastric juice-resistant layer or other lacquers, the use of flavoring and aroma substances and lubricants and customary auxiliaries, which are familiar to the galenical expert, can, of course, also be employed and used in the preparation according to the invention.

Suitable solid administration forms for the corecoat principle according to the invention are, for example, pellets and press-coated tablets. The size of the preparation may vary from 0.5-15 mm.

A particular advantage in the use of pellets lies in the division of the total dose of active compound into a number of subunits (so-called multiple dose) which permits pellets with different thicknesses or with differently composed coatings to be combined in such a way that nearly any desired release profile of the administration form containing the total dose (for example capsule) can be set, for example a linear release of active compound or a continuous increase in the rates of release of active compound or a release of the active compound in pulses. The initial dose can be introduced here, for example, by non-coated active compound cores.

In the case of press-coated tablets, the initial dose can be applied to the placebo coat so that a discontinuous, pulsed release is achieved here.

The lag time set until the release of active compound in the core by eroding away of the coating material causes the desired delayed release effect. The lag time due to eroding away/dissolving of the coating is in this case not decisively influenced by pH.

It may be explicitly indicated therefrom that the delayed release preparation according to the invention differs from the previously known core-coat preparations in that the coating contains no active compound.

The cores of the inventive formulations can be produced by known methods, e.g. by mixing Nifedipine crystals with a specific surface of 1-4 $m^2/g$ with suitable carriers as described in EP-B No. 47 899).

From the prior art, multilayer tablets based on casein matrices have already been described which contain two or three layers which can in each case, in turn, contain active compounds (compare U.S. Pat. No. 3,184,386). The tablets described there contain active compound in the outer coating in contrast to the present invention.

Coated tablets are also described in U.S. Pat. No. 3,558,768 which contain active compounds in slow-release form both in the core and in the coating.

Coated tablets which contain no active compound in the coating material are also described in Il Farmaco, No 3, March 84, 67 f (Conte et al.). However, the release kinetics of these tablets differ considerably from the core-coat principle according to the invention described here: after a lag time, the active compound is continuously released over a long time by zero order kinetics. The coat material serves here as a diffusion barrier but not for setting a discontinuously occurring release of the active compound. In contrast to the core-coating principle according to the present invention, the "reservoir coated tablet" can only be employed in active compounds having a certain minimum water solubility.

Salomon et al. (Pharm. Ind. 41, No. 8, p. 799 f. 1979) also describe coated tablets which contain no active compound in the coat material. These are also "reservoir coated tablets". In principle, that stated above applies.

The diffusion principle described in the previously mentioned examples is not suitable for sparingly soluble dihydropyridines. A delayed release method based on a diffusion principle leads in the case of the sparingly soluble dihydropyridines to extremely slow release of the active compound and to comparatively low levels of drug resulting therefrom.

A further administration form which specifically favorably influences the saturatable first pass effect of psoralens is described in DE No. 3,115,033 A 1. However, the coat material in this case contains active compound. Moreover, the delay until the release of active compound from the core of the coated tablets or pellets is not achieved by the application of high contents of hydrophilic, gel-forming polymers in the coat but by a lacquering of the core/pellet (a thin lacquer film).

In German Offenlegungsschrift 2,651,176, pellets having a controlled release of active compound are described. The formulations described there already differ from the coated preparations according to the invention in that they also contain active compound in the coat. Moreover, the formulations described there can only be obtained by complex methods by continuously applying many layers, whereas the press-coated tablets according to the invention are produced by simple pressing and in the case of the coated pellets, only one layer is continuously applied to the slow-release cores.

By means of the principle of the preparation according to the invention, the customary disadvantages of normal delayed release tablets or pellets and also of previously known multilayer or press-coated tablets and pellets or of preparation forms which are based on the osmotic principle are avoided.

In particular, an adaptation of the release of active compound to diurnal rhythm-dependent biological processes, such as, for example, the blood pressure, can be carried out by means of the coated administration form according to the invention, without having to administer the form at uncustomary times of day. As a further advantage of this form, it may be mentioned that in active compounds which show increased bioavailability on absorption in low sections of the gastrointestinal tract in comparison to absorption in the stomach, this administration form leads to improved bioavailability of the active compound administered. The discontinuous release of this delayed release form caused by the erosion of the coat, which, moreover, takes place independently of pH, must be emphasized. In this way, the release of the sparingly soluble dihydropyridines according to the invention can also be delayed in a suitable manner.

In the case of the coated pellets (medicament form, for example, capsule), the setting of any release kinetics of the active compound (by combination of different coated pellets) may be mentioned as a further additional advantage. In this way, such a delayed release preparation can correspond to the requirements of a previously given active compound as if "made to measure". In regard to the long-existing need with respect to medicament preparation forms having long-lasting action, it is more than surprising that previously nobody has described or produced the simple to prepare and very effective coated medicament form having a slow-release core according to the invention. By means of the present invention, the patient can be placed in the position of only having to administer the medicament once daily which, in particular with long-term therapy, represents a safer and more acceptable type of treatment.

EXAMPLES

Example 1

Figure 1:
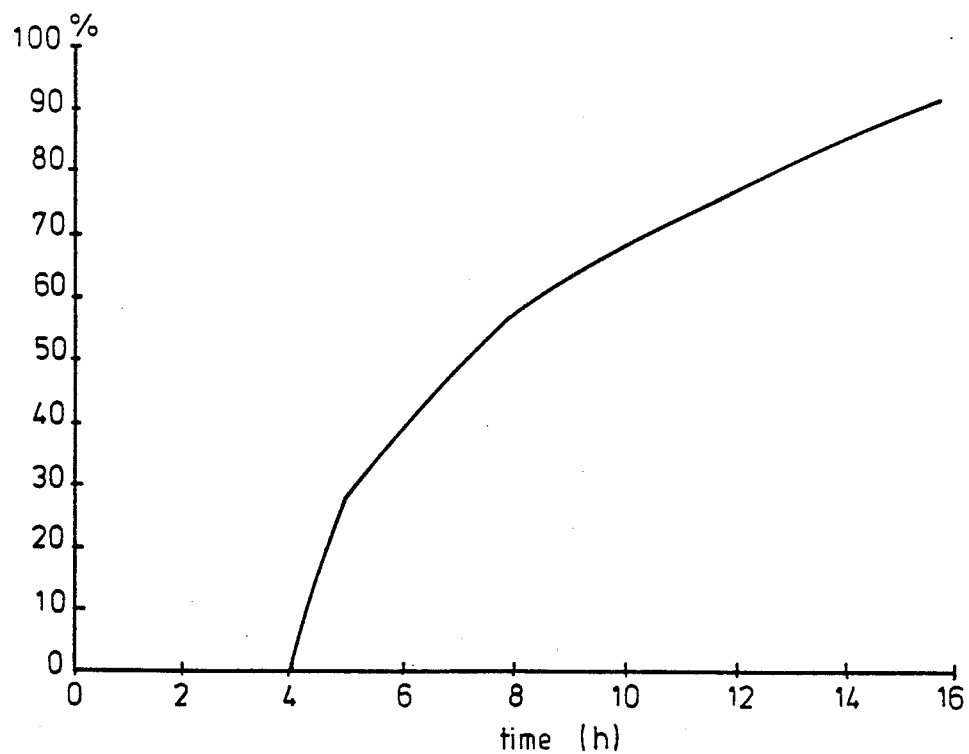
FIG. 1 is a curve showing the principle of the discontinuous release of active compound for Example 1.

| Core: nifedipine 5–50 μm | 20.0 g |
|---|---|
| Avicel | 34.8 g |
| corn starch | 12.0 g |
| lactose | 10.0 g | are mixed and granulated with

| corn starch | 2 g |
|---|---|
| Tween 80 | 1 g | after drying

| magnesium stearate | 0.2 g |
|---|---|

The mixture is pressed in a tablet press to give cores having a weight of 80 mg, size 6 mm diameter. Coating:

| hydroxypropyl-cellulose type L | 31.0 g |
|---|---|
| hydroxypropyl-cellulose type M | 106.0 g |
| lactose, fine | 111.5 g | are granulated using 150 ml of water, and the mixture is subsequently dried. Admixing with

| magnesium stearate | 1.5 g |
|---|---|

The mixture is pressed in a press-coater tablet press to give press-coated tablets of size 9 mm diameter (total tablet weight 330 mg).

Example 2

As Example 1, but a rapidly releasing initial dose of 10 mg of nifedipine in a mixture of auxiliaries customarily used for film lacquering (hydroxypropylmethylcellulose HPMC, PEG 4000) is applied to the press-coated tablet. A further film lacquer which has a light protection function (HPMC, PEG, iron oxide, red) is subsequently applied.

As Example 2, but containing nisoldipine instead of nifedipine.

Example 4

As Example 1, but containing nitrendipine instead of nifedipine.

Example 5

As Example 4 but containing a 3-fold amount of nimodipine instead of nifedipine. Additionally, the initial dose of 30 mg of nimodipine is pressed into the form of a solid solution (co-precipitate) (2 layer coated tablet, not lacquered). An additional light protection layer is unnecessary.

Example 6

|  | (a) | (b) | (c) |
|---|---|---|---|
| Core: nimodipine, microfine | 78 g | 90 g | 88 g |
| hydroxypropylcellulose type L | 15 g | — | — |
| lactose | 5 g | — | — |
| polyvinylpyrrolidone 25 | — | 5 g | 5 g |
| sodium lauryl sulphate | 2 g | 2 g | 2 g |
| Na$_2$SO$_4$ | — | — | 5 g |
| powdered sugar | — | 3 g | — | are mixed and converted by pelletizing with water as a granulating liquid into spherical particles in the diameter range between 0.5–1.5 mm.

Coat

Nimodipine cores and coating powder are simultaneously mixed and metered into a continuously working rotor granulator, and water is sprayed in as a granulating liquid. The coating powder mixture is composed as follows:

Example 6a

| rice starch | 20% |
|---|---|
| castor oil, hydrogenated | 50% |
| hydroxypropylcellulose type M | 30% |

Example 6b

| corn starch pregelatinized | 30% |
|---|---|
| hydroxypropylcellulose type M | 40% |
| hydrogenated castor oil | 30% |

Example 6c

| hydrogenated castor oil | 70% |
|---|---|
| hydroxypropylcellulose type M | 30% |

The coating powder mixture from Examples 6a to 6c is applied to the cores in the following amounts:

Example 6a—250% of the core weight
Example 6b—300 % of the core weight
Example 6c—150 % of the core weight.

It will be appreciated that the instant specification and claims are set forth by way of illustration and not limitation, and that various modifications and changes may be made without departing from the spirit and scope of the present invention.

What is claimed is:

1. A tablet having long-lasting action and a corecoat construction, the core containing at least one sparingly soluble dihydropyridine active compound of the formula I,

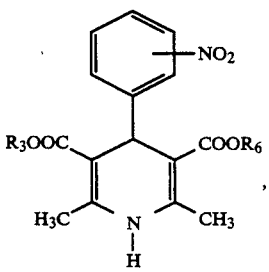

in which $R_3$ and $R_6$ each independently is alkyl having 1 to 4 C-atoms optionally substituted by alkoxy having 1 to 4 C-atoms, in slow-release form, the coat surrounding the core containing no active compound, dissolving slowly and containing a hydrophilic gel forming polymer selected from the group consisting of modified starch, methylcellulose, hydroxypropylmethylcellulose, hydroxypropylcellulose and sodium carboxymethylcellulose, the tablet further coated with a rapid-release initial dose of the active compound mixed with a polymer, the core containing at least 50% of the amount of active compound in delayed release form.

2. A tablet according to claim 1, containing about 1–200 mg of dihydropyridine active compound.

3. A tablet preparation according to claim 1, the core containing at least 50 % of the total dihydropyridine active compound in the slow-release form, and the preparation containing 1–200 mg. of dihydropyridine active compound, the dihydropyridine active compound being selected from the group consisting of nifedipine, nitrendipine, nimodipine and nisoldipine.

* * * * *